US005743910A

United States Patent [19]

Bays et al.

[11] Patent Number: 5,743,910
[45] Date of Patent: Apr. 28, 1998

[54] ORTHOPEDIC PROSTHESIS REMOVAL INSTRUMENT

[75] Inventors: F. Barry Bays, Clearwater; Randall D. Ross; Stephen M. Vajda, both of Largo, all of Fla.

[73] Assignee: Xomed Surgical Products, Inc., Jacksonville, Fla.

[21] Appl. No.: 751,015

[22] Filed: Nov. 14, 1996

[51] Int. Cl.[6] .................................. A61B 17/56; A61F 5/04
[52] U.S. Cl. ................................................ 606/99; 294/63
[58] Field of Search ........................... 606/99, 100, 85, 606/104; 439/769, 770, 772, 774, 765, 822; 294/164, 169, 902, 903; 254/22, 23, 24

[56] References Cited

U.S. PATENT DOCUMENTS

| D. 360,686 | 7/1995 | Kumar et al. |  |
|---|---|---|---|
| 2,503,794 | 4/1950 | Brown | 294/903 |
| 3,857,389 | 12/1974 | Amstutz |  |
| 3,865,419 | 2/1975 | Bowers et al. | 294/903 |
| 4,222,382 | 9/1980 | Antonsson et al. |  |
| 4,642,121 | 2/1987 | Keller |  |
| 4,686,971 | 8/1987 | Harris et al. |  |
| 4,919,153 | 4/1990 | Chin |  |
| 4,919,679 | 4/1990 | Averill et al. |  |
| 4,993,410 | 2/1991 | Kimsey |  |
| 5,064,427 | 11/1991 | Burkinshaw | 606/99 |
| 5,108,402 | 4/1992 | Chin |  |
| 5,156,606 | 10/1992 | Chin |  |
| 5,514,136 | 5/1996 | Richelsoph | 606/99 |

OTHER PUBLICATIONS

Advertisement for Inngmed Universal Modular Femoral Hip Component Extractor, *Orthopedics*, vol. 18, No. 9, 1995 (one page).

Kim Med instructional literature for Stem Extractor described in U.S. Patent No. 4,993,410, date unknown (nine pages).

*Primary Examiner*—Michael Buiz
*Assistant Examiner*—Julian W. Woo

[57] ABSTRACT

An instrument for extracting an orthopedic prosthesis having an elongated shank implanted in bone and defining a first longitudinal axis and a tapered stem projecting from the shank and defining a second longitudinal axis oriented at an oblique angle relative to the first axis includes a lower jaw defining a first opening for receiving the tapered stem, an upper jaw pivotally connected to the lower jaw and defining a second opening in opposed relation to the first opening, and a mechanism for pivoting the upper and lower jaws apart so that, when the tapered stem is received in the first and second openings, at least one of the first and second openings is caused to tilt relative to the second longitudinal axis such that diagonally opposed inside surfaces of the tilted opening contact the tapered stem of the prosthesis at longitudinally spaced locations to secure the instrument to the tapered stem so that an extraction tool can be attached to the instrument and used to exert an extraction force substantially parallel to the first longitudinal axis of the prosthesis. One of a plurality of inserts having differently sized openings is preferably telescopically received in the second jaw opening to accomodate various degrees of taper, and the insert is preferably held in place within the jaw opening by a retainer such as a shoulder screw threaded into the top surface of the upper jaw so that, when the jaws are pivoted apart, inner surfaces of the insert opening will contact the tapered stem to secure the instrument to the prosthesis.

17 Claims, 3 Drawing Sheets

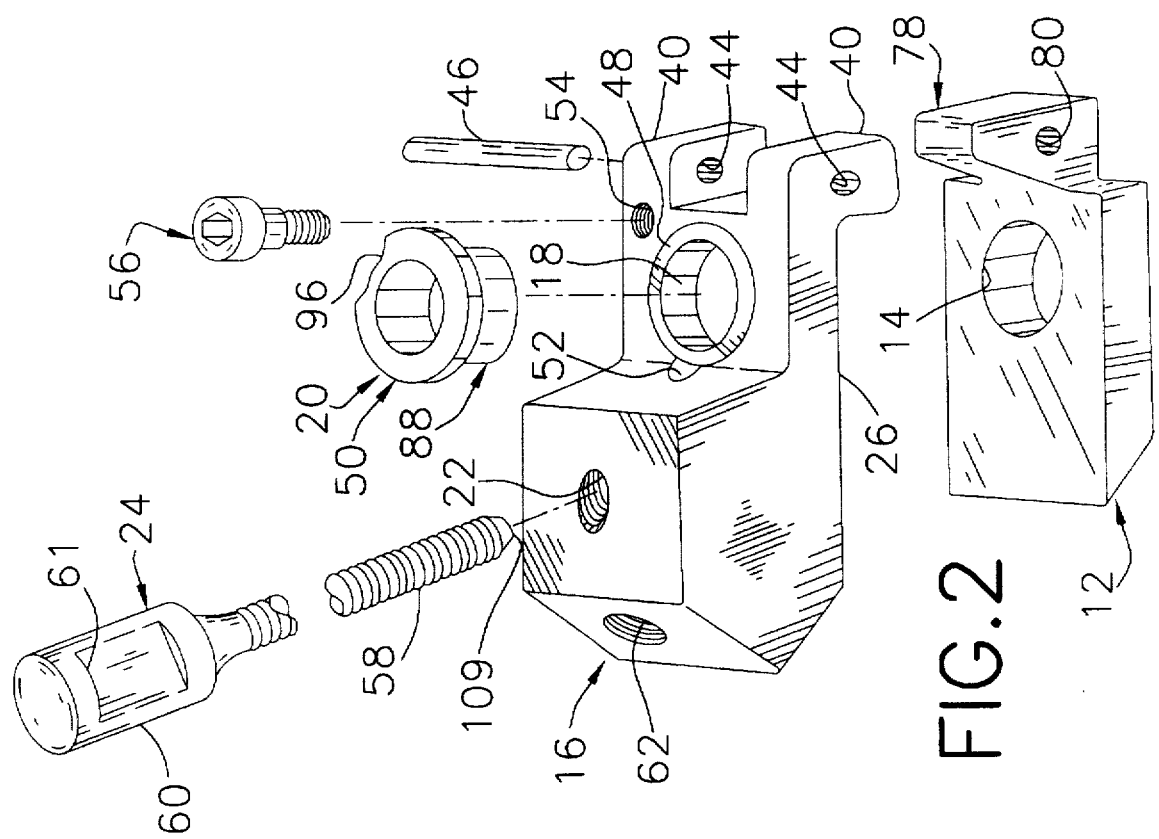
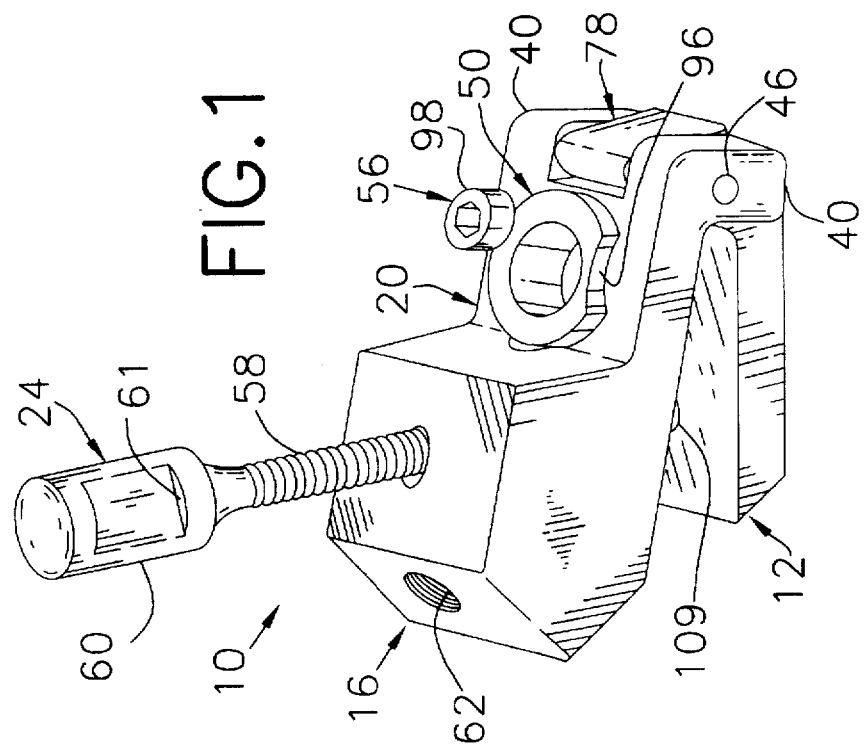

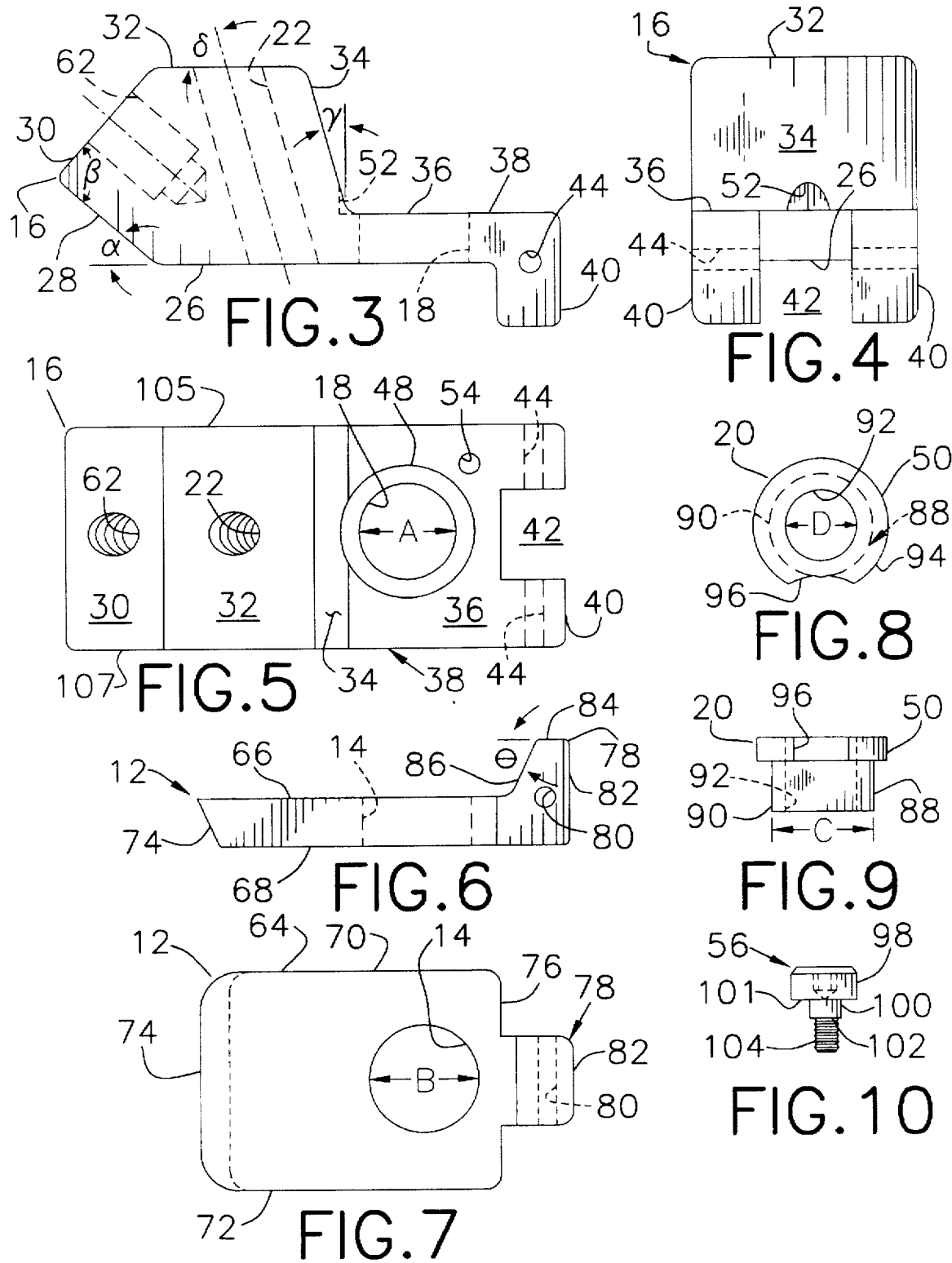

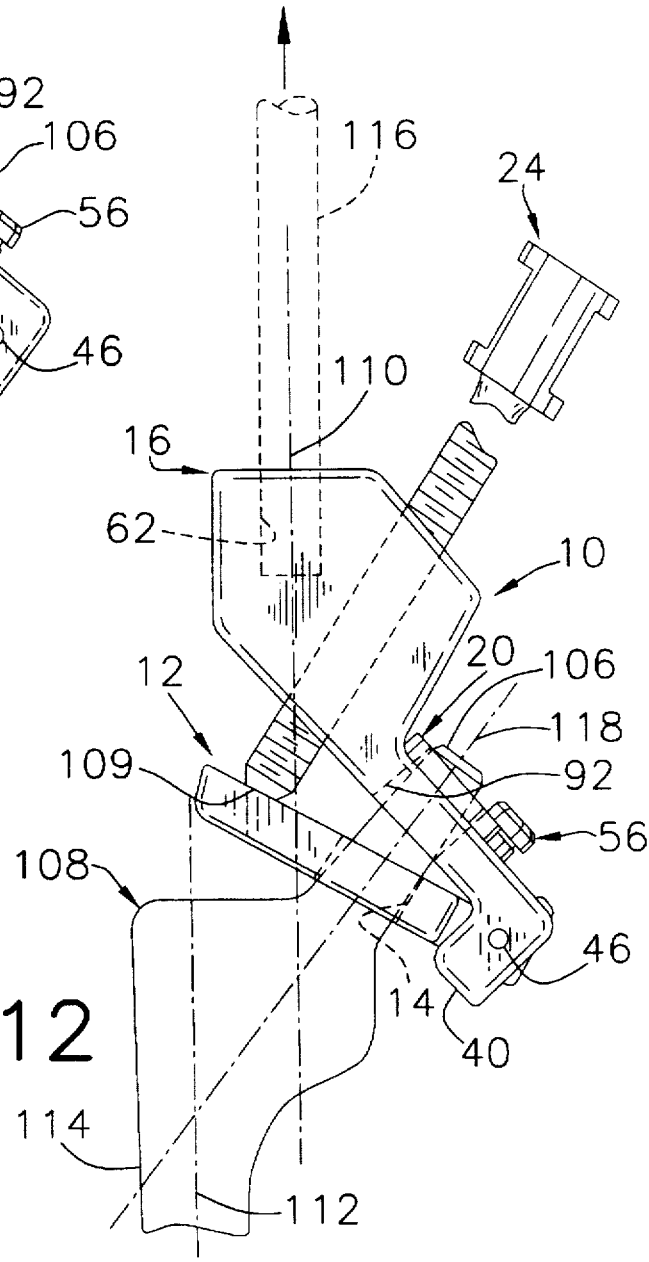

ORTHOPEDIC PROSTHESIS REMOVAL INSTRUMENT

BACKGROUND OF THE INVENTION

1. Field of the Invention

The present invention relates to instruments for removing orthopedic prostheses during surgical procedures and, more particularly, to an instrument for removing an orthopedic prosthesis having a shank implanted in bone and a tapered stem projecting from the shank at an oblique angle.

2. Discussion of the Related Art

Various articulating joints of the body, such as the joints of the hips, have anatomical ball and socket connections between bones of the joints providing a wide range of motion. The hip joint, for example, includes a socket or acetabulum in the pelvis and a femoral head or ball at an upper end of the femur or thigh bone received in the acetabulum. Where natural articulating joints are congenitally defective or become degraded due to disease or injury, prosthetic or artificial ball and socket components are commonly implanted in the body to replace the natural ball and socket structure of the joints.

In total hip replacement surgery, for example, a femoral component having a spherical head or ball thereon is implanted in the femur and an acetabular component in the form of a cup-shaped socket is affixed to the acetabulum with the head or ball of the femoral component rotatably received in the socket to recreate the natural articulation of the hip joint. The femoral component of the prosthesis is typically made of a tough metal (e.g., 60% cobalt by composition) and includes a shaft or shank having an elongate configuration for insertion into a surgically-created cavity in the femur and a stem projecting upwardly from the shank at an oblique angle for receiving the spherical head or ball of the prosthesis. The cavity in the femur is specifically shaped to snugly receive the shank of the prosthesis, with bone cement often being used between the wall of the cavity and the shank to achieve a tighter fit. After surgery, it will be appreciated that tissue growth around the shank of the prosthesis can further tighten the fit between the prosthesis and the femur.

Over time, a significant proportion of artificial joints will fail or become infected requiring revision surgery to remove one or both of the prosthetic components; however, the tight fit of the femoral component in the femur makes the removal procedure difficult. While most of the femoral components currently available have some type of tapered stem which can be used to grasp the prosthesis for removal, the size and shape of the taper tends to vary dependent upon the manufacturer of the prosthesis, so that no single instrument has been capable of grasping different prostheses by the stem without causing some type of damage.

One approach, exemplified by U.S. Pat. No. 4,993,410 to Kimsey, involves the use of a coupling member including an arm with a pair of jaws at one end defining an opening therebetween for receiving the stem of a prosthesis and an internally threaded hole formed at an opposite end of the arm for receiving the threaded portion of a slide bar. One of a series of differently sized sleeves having substantially cylindrical outer diameters complementary to the opening in the arm and generally frustoconical inner surfaces tapered for complementary fit with a particular stem is inserted into the opening to provide a precise fit with the particular stem. In use, the coupling member is positioned such that the stem is inserted within the sleeve and the slide bar is oriented parallel to the longitudinal axis of the shank. A bolt is then tightened to close the jaws against the sleeve so that the sleeve is clamped around the stem, and a weight is moved rapidly in an upward direction along the slide bar into a striking head at the upper end of the bar to cause the coupling member to transmit an upward lifting force on the shank of the prosthesis via the stem. Repeated impact of the weight with the striking head urges the prosthesis upward and out of the femur.

Since the stem of the prosthesis is oriented at an oblique angle relative to the shank, it will be appreciated that the lifting force applied to the stem parallel to the longitudinal axis of the shank will have a component that acts along the longitudinal axis of the stem in the direction of the taper. A disadvantage of the instrument described above is that the inner surface of the sleeve must match the taper of the stem exactly in order to achieve a clamping force sufficient to overcome the force component acting along the stem in order to prevent the instrument from sliding off the stem. As a result, different sleeves must be manufactured for each type of prosthesis and surgeons must have a large number of such sleeves on hand to achieve a perfect match with the taper of the particular prosthesis being removed.

SUMMARY OF THE INVENTION

Accordingly, it is a primary object of the present invention to overcome the above mentioned disadvantages of the prior art and to improve instruments of the type used to extract a prosthesis having an elongated shank implanted in bone and a tapered stem projecting from the shank at an oblique angle.

Another object of the present invention is to reliably grip the stem of a variety of different prostheses for removal with a single instrument by pivoting jaws of the instrument apart with the stem of a prosthesis positioned within openings formed in opposed relation through the jaws.

Yet another object of the present invention is to increase the gripping force applied to the stem of a prosthesis by a prosthesis removal instrument by pivoting jaws of the instrument apart about a pivot axis on one side of a pair of stem-receiving openings formed in opposed relation through the jaws using a force applied to the jaws on an opposite side of the stem-receiving openings.

Some of the advantages of the present invention over the prior art are that the instrument is manually adjustable to fit a wide variety of stemmed prostheses, including most currently available femoral hip components with fully tapered stems, without the need for taper-matching components, that the instrument can be used with conventional impact devices such as sliding weights and slotted hammers, that the instrument provides a mechanical advantage allowing larger gripping forces to be applied to the stem of a prosthesis for improved reliability, that the instrument simplifies removal of stemmed prostheses without damaging the prostheses in a manner preventing their reuse, and that the instrument can be sterilized for reuse or disposable for single patient use as desired.

These and other objects, advantages and benefits are achieved with the present invention as generally characterized in an instrument for extracting an orthopedic prosthesis having an elongated shank implanted in bone and defining a first longitudinal axis and a tapered stem projecting from the shank and defining a second longitudinal axis oriented at an oblique angle relative to the first axis, the instrument including a lower jaw defining a first opening for receiving the tapered stem, an upper jaw pivotally connected to the lower jaw and defining a second opening in opposed relation to the first opening, and means for pivoting the upper and lower jaws apart so that, when the tapered stem is received in the first and second openings, at least one of the first and second openings is caused to tilt relative to the second longitudinal axis such that diagonally opposed inside surfaces of the tilted opening contact the tapered stem of the prosthesis at longitudinally spaced locations to secure the instrument to the tapered stem so that an extraction tool can be attached to the instrument and used to exert an extraction force substantially parallel to the first longitudinal axis of the prosthesis. One of a plurality of inserts having differently sized openings is preferably telescopically received in the second jaw opening to accommodate various degrees of taper, and the insert is preferably held in place within the jaw opening by a retainer such as a shoulder screw threaded into the top surface of the upper jaw so that, when the jaws are pivoted apart, inner surfaces of the insert opening will contact the tapered stem to secure the instrument to the prosthesis.

Another aspect of the present invention is generally characterized in a method of extracting an orthopedic prosthesis having an elongated shank implanted in bone and defining a first longitudinal axis and a tapered stem projecting from the shank and defining a second longitudinal axis oriented at an oblique angle relative to the first axis, the method including the steps of placing the tapered stem through aligned openings formed in pivoted jaws, pivoting the jaws apart to cause inner surfaces of the openings to grippingly contact the tapered stem, and exerting an extraction force parallel to the first axis via the pivoted jaws. One of a plurality of inserts having differently sized openings is preferably chosen to accommodate the taper of the stem and is placed in one of the jaw openings prior to positioning the stem in the jaw openings so that, when the jaws are pivoted apart, inner surfaces of the insert opening will grippingly contact the tapered stem. Pivoting the jaws apart may, for example, include tightening a screw threaded through one of the jaws to bear against the opposed jaw. The extraction force can be applied to the prosthesis via the removal instrument by attaching a rod to the upper jaw of the instrument parallel to the first axis and sliding an impact device such as a sliding weight or slotted hammer along the rod into an impact receiving structure or head at the top of the rod.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 1 is a perspective view of an orthopedic prosthesis removal instrument according to the present invention.

FIG. 2 is an exploded perspective view of the orthopedic prosthesis removal instrument shown in FIG. 1.

FIG. 3 is a side view, in elevation, of the upper jaw of the orthopedic prosthesis removal instrument of FIG. 1.

FIG. 4 is a rear view, in elevation, of the upper jaw of the orthopedic prosthesis removal instrument of FIG. 1.

FIG. 5 is a top plan view of the upper jaw of the orthopedic prosthesis removal instrument of FIG. 1.

FIG. 6 is a side view, in elevation, of a lower jaw of the orthopedic prosthesis instrument of FIG. 1.

FIG. 7 is a top plan view of the lower jaw shown in FIG. 6.

FIG. 8 is a top plan view of an insert for use with the orthopedic prosthesis removal instrument according to the present invention.

FIG. 9 is a side view, in elevation, of the insert shown in FIG. 8.

FIG. 10 is a side view, in elevation, of a shoulder screw for use with the orthopedic prosthesis removal instrument according to the present invention.

FIGS. 11 and 12 are side views, partly broken, illustrating use of the orthopedic prosthesis instrument to extract a femoral hip component having a fully tapered stem.

DETAILED DESCRIPTION OF THE PREFERRED EMBODIMENT

The orthopedic prosthesis removal instrument of the present invention is described hereinafter for use in extracting the femoral component of a prosthetic hip joint having a shank or shaft implanted in the femur and a tapered stem projecting from the shank at an oblique angle. It will be understood, however, that the instrument of the present invention can be used to extract any type of orthopedic prosthesis having a shank implanted in bone and a tapered stem projecting from the shank at an oblique angle.

An instrument 10 for extracting an orthopedic prosthesis in accordance with the present invention, as shown in FIGS. 1 and 2, includes a lower jaw 12 with an opening 14 for receiving the tapered stem of a prosthesis, an upper jaw 16 pivotally connected to the lower jaw and having an opening 18 for receiving a hollow insert or sleeve 20 and a threaded bore 22 receiving a tightening screw 24 for engaging the lower jaw to pivot the upper and lower jaws apart.

Referring to FIGS. 3–5, upper jaw 16 has a bottom surface or face 26 extending from a rear end of the upper jaw to a forwardly projecting dihedral face composed of a first upwardly angled surface 28 extending forwardly from the bottom surface at an acute angle α (e.g., about 41°) and a second upwardly angled surface 30 extending rearwardly from an upper edge of the first surface at a dihedral angle β (e.g., about 86°) to a top surface or face 32 parallel to bottom surface 26. Top surface 32 extends rearwardly from an upper edge of the forwardly projecting dihedral face to an upper edge of a rearwardly facing back surface or face 34. Back surface 34 extends downwardly from top surface 32 at a slight angle γ (e.g., about 15°) toward the rear of the upper jaw and intersects the upper surface 36 of a plate-like extension 38 extending rearwardly of the back surface in parallel relation to top and bottom surfaces 32 and 26. A pair of laterally spaced lugs 40 of generally rectangular configuration project rearwardly from the plate-like extension and turn downwardly in a direction perpendicular to upper surface 36 to define a pocket or gap 42 therebetween. Axially aligned pivot openings 44 are formed through lugs 40 in a direction parallel to bottom surface 26 and perpendicular to the longitudinal axis of the upper jaw to accommodate a cylindrical pin or pivot 46.

Opening 18 extends through plate-like extension 38 of the upper jaw in perpendicular relation to upper surface 36 and is of circular cylindrical configuration with a diameter A (e.g., about 0.656 inches) to receive insert 20. An annular portion of the upper surface surrounding the opening is spot faced at 48 so that an outwardly extending flange or rim 50 of circular configuration at the top of the insert is properly seated when the insert is received within the upper jaw opening. Spot faced portion 48 is of slightly greater diameter than the insert flange (e.g., about 0.813 inches) and is shown extending into back surface 34 to form a curved recess 52 therein providing clearance for the insert flange to lay flat against the upper surface of the jaw extension. A small hole 54 diagonally spaced from opening 18 between the spot faced portion of the upper surface and one of the rear lugs is internally threaded (e.g., with 10-32 threads) to receive a shoulder screw 56 for engaging the insert flange to retain or lock the insert in place within the upper jaw opening as will be discussed in greater detail below.

Threaded bore 22 extends downwardly in a slightly rearward direction, looking at FIG. 3, through upper jaw 16 from top surface 32 to bottom surface 26 at an angle δ (e.g., about 75°) relative to the top surface to receive tightening screw 24 which, as seen in FIGS. 1 and 2, includes a threaded shank 58 (e.g., with ⅜-16 UNC-2A threads) and a cylindrical head 60 having a diameter greater than the shank (e.g., about 0.75 inches) and parallel rectangular slots or depressions 61 formed on diametrically opposed sides of the head to receive the jaws of a wrench or other tool for turning the screw. A second threaded bore 62 extends perpendicularly into the second upwardly angled surface 30 of the forward facing dihedral face of the upper jaw and is configured (e.g., with ⅜-16 UNC-2B threads) to receive the lower end of an extraction tool such as, for example, a conventional slap hammer rod.

Referring to FIGS. 6 and 7, lower jaw 12 includes a generally rectangular plate-like portion 64 having top and bottom surfaces or faces 66 and 68 with laterally opposed sides 70 and 72 and front and rear edges 74 and 76, and a lug 78 projecting rearwardly from a center of the rear edge of the plate-like portion and extending upwardly in a direction generally perpendicular to the top surface of the plate to fit in the gap 42 between lugs 40 of the upper jaw. A pivot opening 80 extends through lug 78 perpendicular to the longitudinal axis of the lower jaw and parallel to top and bottom surfaces 66 and 68 at an elevation to be axially aligned with openings 44 in the upper jaw lugs when the upper and lower jaws are assembled together as shown, for example, in FIG. 1. Lug 78 is generally trapezoidal with a rear surface or face 82 extending upwardly from bottom surface 68 at a right angle, an upper surface or face 84 extending forwardly from the top of the rear surface parallel to the bottom surface and a front surface or face 86 extending downwardly from the upper surface at an angle θ (e.g., about 62°) toward the forward end of the jaw such that, when the lower jaw lug is disposed within the gap between the upper jaw lugs with their respective pivot openings aligned, sufficient angular clearance will be provided between the front surface of the lower jaw lug and the rear edge of the upper jaw extension to permit unobstructed pivotal movement of the lower jaw lug within the pocket or gap defined between the upper jaw lugs. Opening 14 is formed through the plate-like portion of the lower jaw in perpendicular relation to the top and bottom surfaces and in opposed or aligned relation to opening 18 in the upper jaw when the upper and lower jaws are pivotally connected. The opening 14 is shown having a circular cylindrical configuration with a diameter B (e.g., about 0.562 inches) for receiving the tapered stem of an orthopedic prosthesis. Front edge 74 of the lower jaw extends downwardly in the rearward direction from top surface 66 at an acute angle (e.g., about 75°) and includes rounded corners to reduce the risk of trauma to surrounding tissue when the instrument is secured to a prosthesis.

As best seen in FIGS. 8 and 9, insert 20 includes a hollow cylindrical sleeve 88 with an outwardly extending rim or flange 50 extending radially outward from the top of the sleeve in a direction perpendicular to a longitudinal axis of the sleeve. Sleeve 88 has an outer surface 90 of circular cylindrical configuration with an outer diameter C (e.g., about 0.655 inches) to slidingly fit within opening 18 in upper jaw 16 and an inner surface or opening 92 of circular cylindrical configuration with an inner diameter D (e.g., between about 0.45 and about 0.55 inches) for receiving the stem of a prosthesis with some clearance, the insert opening diameter D being smaller than the diameter B of lower jaw opening 14 to compensate for the taper of the stem. The diameter of the insert opening is chosen dependent upon the particular prosthesis being removed, with each insert diameter accepting a range of tapers so that, for example, most currently available femoral components can be removed using one of only three inserts having inner diameters of, for example, 0.450, 0.500 and 0.540 inches, respectively. Rim or flange 50 of the insert includes an outer peripheral edge 94 of generally circular configuration with a pair of intersecting circular cut-outs defining a notch 96 with a slightly scalloped configuration providing clearance for the head of retaining screw 56.

As best seen in FIG. 10, screw 56 includes a socket head 98 for receiving a tightening tool such as, for example, an Allen wrench, a spacer portion 100 of generally cylindrical configuration extending downwardly, looking at FIG. 10, from a bottom 101 of the socket head to a radial step or shoulder 102 connecting the spacer portion with a threaded portion 104 of the screw. Spacer portion 100 preferably has an axial length (e.g., about 0.125 inches) equal to or slightly greater than the thickness of insert flange 50 so that, when the insert flange is seated on top surface 36 of upper jaw 16, screw 56 can be tightened down completely with shoulder 102 of the spacer portion abutting top surface 36 and bottom 101 of the head overlapping the insert flange to retain the insert within opening 18 as shown, for example, in FIG. 1.

Tightening screw 24, insert 20 and upper and lower jaws 16 and 12 can be formed in any suitable manner using any suitable material but are preferably machined from Type 440A/440C stainless steel stock, heat treated to full hard condition in a controlled atmosphere and then tempered to a final Rockwell C hardness of between about 50 and about 53. Shoulder screw 56 and pin 46 can also be formed of any suitable material but are preferably formed of 17-4 precipitation hardened stainless steel (A.S.T.M. A564) with the screw preferably being heat treated to condition H900.

The prosthesis extracting instrument 10 is assembled by positioning upper jaw 16 on top of lower jaw 12 with lower jaw lug 78 between upper jaw lugs 40. Pivot openings 44 in the upper jaw lugs should be aligned with opening 80 in the lower jaw lug so that pin 46 can be passed through the openings with opposite axial ends protruding slightly from lateral sides 105 and 107 of the upper jaw. The protruding axial ends of the pin are then peened until flush with the lateral sides of the upper jaw to prevent removal of the pin from the openings and to establish a pivot axis about which the lower jaw can rotate. With upper and lower jaws 16 and 12 of the instrument 10 pivotally connected, tightening screw 24 is threaded into bore 22 part way so as not to force the upper and lower jaws apart, and shoulder screw 56 is threaded into blind hole 54 until spacer 100 abuts upper surface 36 of the plate-like portion or extension of the upper jaw.

In use, an insert is chosen having an opening with a diameter suitable for receiving the tapered stem of an implanted femoral component, for example by placing inserts with differently sized openings over the stem until an insert with an appropriately sized opening is found. Once an insert 20 has been chosen, the insert is grasped by the flange 50 and moved such that the lower cylindrical sleeve portion 88 of the insert is positioned above opening 18 in the upper jaw and cut-out 96 in the flange is oriented toward the head of shoulder screw 56 as shown, for example, in FIG. 2. The insert 20 is then lowered into opening 18 until insert flange 50 is seated on the spot-faced portion of upper surface 36 of the upper jaw, with cut-out 96 allowing the flange to clear the outwardly protruding head 98 of the shoulder screw as the insert is lowered. The insert 20 is then rotated about its longitudinal axis until the cut-out in flange 50 is angularly spaced from the head of shoulder screw 56 so that the bottom of the screw head overlaps and abuts a solid portion of the flange to prevent the insert from being inadvertently removed from the jaw.

With tightening screw 24 threaded only part of the way through upper jaw 16, the tip 109 of the screw is vertically spaced from or flush with bottom surface 26 of the upper jaw and instrument 10 is in an unexpanded or collapsed position or condition where the bottom surface of the upper jaw is able to lay flat against top surface 66 of lower jaw 12. Instrument 10 is grasped in the collapsed position and placed over the tapered stem 106 of a femoral component 108, as shown in FIG. 11, so that the tapered stem extends through opening 14 in lower jaw 12 and protrudes from the opening 92 defined by insert 20 in upper jaw 16. Because the stem is tapered, the space between the stem and inner surfaces of the openings increases in an upward direction along the longitudinal axis of the stem allowing the instrument to rock somewhat and slide up and down on the stem in the collapsed position.

Instrument 10 is secured to the tapered stem by turning screw 24, for example with a wrench, to cause the tip 109 of the screw to advance downwardly through bore 22 into contact with the top surface of lower jaw 12. Screw 24 forces the lower jaw to pivot about pin 46 in a counterclockwise direction, looking at FIG. 12, and to tilt relative to the tapered stem so that, when viewed from the side as shown, diagonally opposed inner surfaces of opening 14 are wedged against the stem at spaced locations along the longitudinal axis of the stem to prevent the lower jaw from moving. With lower jaw wedged against the stem, further tightening of screw 24 causes upper jaw 16 to rotate clockwise, looking at FIG. 12, until diagonally opposed inner surfaces of opening 92 in the insert 20 are wedged against the stem to prevent the upper jaw from moving. Continued tightening of screw 24 causes upper and lower jaws of the instrument to pivot about points of contact with the tapered stem, and it will be appreciated that the jaws of the instrument act like lever arms to provide a mechanical advantage. The instrument is now in an expanded position or condition with upper and lower jaws pivoted apart and the longitudinal axis 110 defined by extractor hole 62 in the upper jaw oriented substantially parallel or aligned with the longitudinal axis 112 defined by the shank 114 of the prosthesis.

With instrument 10 in the expanded position, an extraction tool, such as the slide rod shown by broken lines at 116 in FIG. 12, can be threaded into hole 62 and used to exert an extraction force in the direction of longitudinal axis 110, for example by sliding a weight along the rod into an enlarged head at the upper end of the handle or by striking the head with a slotted hammer in an upward direction. The extractor hole 62 in the upper jaw is angled so that the rod 116 will be in line with the longitudinal axis 112 of the shank to allow for maximum in-line mechanical advantage when hammering out a well-fixed prosthesis. Since the impact force is being applied via the obliquely angled stem, a component of the force will be directed along the longitudinal axis 118 of the stem in the direction of the taper; however, because the instrument provides a mechanical advantage, very large gripping pressures can be produced which prevent the instrument from slipping off the stem.

After extracting the prosthesis 108, the instrument 10 can be removed from the stem of the prosthesis by loosening screw 24 to cause the jaws of the instrument to return to the collapsed condition. In the collapsed condition, inner surfaces of the lower jaw and insert openings are not wedged against the stem allowing the instrument to easily slide off the stem.

From the above, it will be appreciated that the orthopedic prosthesis removal instrument according to the present invention permits a variety of different prostheses to be gripped by the stem for removal without the need of having to closely match the taper of each stem. The instrument includes a pair of pivotally connected jaws with opposed openings for receiving the stem of a prosthesis and means for pivoting the jaws apart to cause one or both of the jaws to tilt relative to the stem thereby gripping the stem and allowing an extraction tool to be attached to the instrument to exert an extraction force on the prosthesis.

Upper and lower jaws of the instrument can have any suitable configuration for receiving the stem of a prosthesis and pivoting apart to grip the stem. For example, openings can be formed through the jaws in opposed relation perpendicular to upper and lower surfaces of the jaws, or the openings can be oriented at any suitable angle relative to one or both of the upper and lower surfaces of each jaw. Furthermore, the openings formed through the jaws can be through-holes or slots and can have any configuration in transverse cross-section including, but not limited to, elliptical, polygonal, tapered or combined cross-sectional configurations. The jaws can be pivotally connected anywhere along their respective lengths so that, for example, the pivot axis can be disposed at an extreme axial end of the instrument as shown or at any position intermediate opposite axial ends of the instrument as desired. The pivot means can be a screw threaded through one of the upper and lower jaws, multiple screws threaded through one or both of the jaws, or any other type of mechanism capable of applying a force to pivot the jaws apart. The pivot force can be applied to the jaws between the pivot axis and the stem, on a side of the stem opposite the pivot axis, or on a side of the pivot axis opposite the stem (in the case of the pivot axis being disposed intermediate opposite axial ends of the instrument). The opening in the upper jaw is preferably slightly larger than the opening in the lower jaw to accommodate a removable insert having an opening therein for receiving an upper end of the stem, with the insert opening typically being somewhat smaller than the opening in the lower jaw to compensate for the taper of the stem. The insert opening is preferably cylindrical in configuration but can be tapered or have any other configuration to grippingly engage the stem when pivoting with the instrument. While a shoulder screw is shown engaging a flange at the top of the insert to retain the insert in the opening in the upper jaw, it will be appreciated that any suitable retaining mechanism can be used including, but not limited to, rotating locks, clips and mechanical detents. It will also be appreciated that any of the threaded screws described herein can be provided with gripping surfaces and/or features that mate cooperatively with tools such as, for example, wrenches, screw drivers and pliers to permit tightening of the screws.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An instrument for extracting an orthopedic prosthesis having an elongated shank implanted in bone and defining a first longitudinal axis and a tapered stem projecting from the shank and defining a second longitudinal axis oriented at an oblique angle relative to the first axis, said instrument comprising a lower jaw defining a first opening for receiving the tapered stem;

an upper jaw pivotally connected to said lower jaw and defining a second opening in opposed relation to said first opening; and pivot means for forcing said upper and lower jaws to pivot apart so that, when the tapered stem is received in said first and second openings, at least one of said first and second openings is caused to tilt relative to the second longitudinal axis such that diagonally opposed inside surfaces of said tilted opening contact the tapered stem of the prosthesis at longitudinally spaced locations to secure said instrument to the tapered stem so that an extraction tool can be attached to the instrument and used to exert an extraction force substantially parallel to the first longitudinal axis of the prosthesis.

2. An instrument as recited in claim 1 and further comprising an insert telescopically received in said second opening for receiving said tapered stem.

3. An instrument as recited in claim 2 and further comprising means for retaining said insert in said second opening.

4. An instrument as recited in claim 3 wherein said insert includes a hollow portion defining a cylindrical inner surface and a rim that rests on an upper surface of said upper jaw to prevent said insert from passing through said jaw.

5. An instrument as recited in claim 4 wherein said rim includes a cut-out configured to clear said retaining means when said insert is placed in said opening in said upper jaw, said insert being rotatable within said upper jaw opening to cause said retaining means to engage said rim.

6. An instrument as recited in claim 5 wherein said retaining means includes a shoulder screw threadedly coupled with said upper jaw and including a head having a bottom engaging said insert rim to retain said insert in said upper jaw opening when said cut-out is angularly spaced from said screw head.

7. An instrument as recited in claim 1 wherein said pivot means includes a threaded bore defined through said upper jaw and a tightening screw disposed in said threaded bore to bear against said lower jaw when tightened.

8. An instrument as recited in claim 1 wherein said upper jaw includes means for attaching an extraction tool parallel to the first longitudinal axis of the orthopedic prosthesis.

9. An instrument as recited in claim 8 wherein said attaching means includes a second threaded bore formed in said upper jaw.

10. An instrument as recited in claim 1 wherein said upper and lower jaws pivot relative to one another about a pivot axis disposed substantially perpendicular to the second longitudinal axis of the orthopedic prosthesis.

11. An instrument as recited in claim 10 wherein said means applies a force to said upper and lower jaws to pivot said jaws apart and wherein said first and second openings are disposed between said pivot axis and the point of application of said pivot force.

12. A method of extracting an orthopedic prosthesis having an elongated shank implanted in bone and defining a first longitudinal axis and a tapered stem projecting from the shank and defining a second longitudinal axis oriented at an oblique angle relative to the first axis, said method comprising the steps of placing the tapered stem through aligned openings formed in pivoted jaws;

pivoting the jaws apart to cause inner surfaces of the openings to grippingly contact the tapered stem; and exerting an extraction force parallel to the first axis via the pivoted jaws.

13. A method as recited in claim 10 and further comprising, prior to placing the tapered stem through the aligned openings in the jaws, the steps of choosing an insert with an opening to receive the tapered stem and placing the insert in one of the openings in the pivoted jaws.

14. A method as recited in claim 10 wherein said pivoting step includes tightening a screw threaded through one of the jaws to bear against the opposed jaw causing the jaws to pivot apart.

15. A method as recited in claim 10 wherein said step of exerting an extraction force includes attaching a rod to the upper jaw parallel to the first axis and sliding an impact device along the rod into an impact receiving structure at the top of the rod.

16. An instrument for extracting an orthopedic prosthesis having an elongated shank implanted in bone and defining a first longitudinal axis and a tapered stem projecting from the shank and defining a second longitudinal axis oriented at an oblique angle relative to the first axis, said instrument comprising a lower jaw defining a first opening for receiving the tapered stem;

an upper jaw pivotally connected to the lower jaw and defining a second opening in opposed relation to said first opening; and a tightening device coupled with said jaws and operable to move said jaws pivotally relative to one another so that, when the tapered stem is received in said first and second openings, at least one of said first and second openings is caused to tilt relative to the second longitudinal axis such that an inside surface of said tilted opening contacts the tapered stem of the prosthesis to secure said instrument to the tapered stem so that an extraction tool can be attached to the instrument and used to exert an extraction force substantially parallel to the first longitudinal axis of the prosthesis.

17. An instrument as recited in claim 16 wherein said tightening device includes a screw threadedly received within an opening formed through one of said jaws.

* * * * *